(12) United States Patent
Ogilvie (10) Patent No.: US 8,470,045 B2
(45) Date of Patent: Jun. 25, 2013

(54) ENDPLATE FOR AN INTERVERTEBRAL PROSTHESIS AND PROSTHESIS INCORPORATING THE SAME

(75) Inventor: William F. Ogilvie, Austin, TX (US)

(73) Assignee: K2M, Inc., Leesburg, VA (US)

( * ) Notice: Subject to any disclaimer, the term of this patent is extended or adjusted under 35 U.S.C. 154(b) by 118 days.

(21) Appl. No.: 12/990,935

(22) PCT Filed: May 5, 2009

(86) PCT No.: PCT/US2009/042896
§ 371 (c)(1),
(2), (4) Date: Nov. 3, 2010

(87) PCT Pub. No.: WO2009/137518
PCT Pub. Date: Nov. 12, 2009

(65) Prior Publication Data
US 2011/0060416 A1   Mar. 10, 2011

Related U.S. Application Data

(60) Provisional application No. 61/050,554, filed on May 5, 2008.

(51) Int. Cl.
*A61F 2/44* (2006.01)
(52) U.S. Cl.
USPC ............................................... 623/17.16
(58) Field of Classification Search
USPC ........................................... 623/17.16
See application file for complete search history.

(56) References Cited

U.S. PATENT DOCUMENTS

| 3,867,728 A | * | 2/1975 | Stubstad et al. | ........... 623/17.16 |
| 3,875,595 A | | 4/1975 | Froning | |

(Continued)

FOREIGN PATENT DOCUMENTS

| DE | 42 19 939 | 12/1993 |
| DE | 201 11 479 | 11/2001 |

(Continued)

OTHER PUBLICATIONS

Hellier WG et al., Spine 1992, 127(6 Suppl.): Ss86-96.

(Continued)

*Primary Examiner* — Ellen C Hammond
*Assistant Examiner* — Stuart S Bray
(74) *Attorney, Agent, or Firm* — Miles & Stockbridge P.C.

(57) ABSTRACT

An endplate for an intervertebral disc prosthesis includes: a plate member having a generally planar rim for contacting the peripheral cortical rim of a vertebral body, and an elevated region within the rim having an anterior region and a posterior region, wherein the anterior region of the elevated region is preferably recessed with respect to the posterior region and is treated to promote bone ingrowth. The endplate may be provided with a medial fin extending partway from the anterior edge of the endplate toward the posterior edge of the endplate.

37 Claims, 10 Drawing Sheets

U.S. PATENT DOCUMENTS

| | | | |
|---|---|---|---|
| 4,349,921 A | 9/1982 | Kuntz | |
| 4,759,766 A | 7/1988 | Buettner-Janz | |
| 4,759,769 A | 7/1988 | Hedman | |
| 4,772,287 A | 9/1988 | Ray et al. | |
| 4,863,477 A * | 9/1989 | Monson | 623/17.12 |
| 4,904,260 A | 2/1990 | Ray et al. | |
| 4,911,718 A * | 3/1990 | Lee et al. | 623/17.15 |
| 4,932,969 A | 6/1990 | Frey et al. | |
| 4,946,378 A | 8/1990 | Hirayama et al. | |
| 5,002,576 A | 3/1991 | Fuhrmann | |
| 5,047,055 A * | 9/1991 | Bao et al. | 623/17.16 |
| 5,071,437 A * | 12/1991 | Steffee | 623/17.16 |
| 5,123,926 A | 6/1992 | Pisharodi | |
| 5,171,281 A | 12/1992 | Parsons et al. | |
| 5,190,547 A | 3/1993 | Barber et al. | |
| 5,192,326 A * | 3/1993 | Bao et al. | 623/17.12 |
| 5,258,031 A | 11/1993 | Salib et al. | |
| 5,306,308 A * | 4/1994 | Gross et al. | 623/17.16 |
| 5,306,309 A | 4/1994 | Wagner et al. | |
| 5,314,477 A * | 5/1994 | Marnay | 623/17.15 |
| 5,314,478 A | 5/1994 | Oka | |
| 5,320,644 A | 6/1994 | Baumgartner | |
| 5,370,697 A | 12/1994 | Baumgartner | |
| 5,401,269 A * | 3/1995 | Buttner-Janz et al. | 623/17.15 |
| 5,458,642 A | 10/1995 | Beer et al. | |
| 5,458,643 A | 10/1995 | Oka | |
| 5,514,180 A | 5/1996 | Heggeness et al. | |
| 5,534,028 A | 7/1996 | Bao et al. | |
| 5,534,030 A * | 7/1996 | Navarro et al. | 623/17.15 |
| 5,545,229 A * | 8/1996 | Parsons et al. | 623/17.15 |
| 5,556,431 A * | 9/1996 | Buttner-Janz | 623/17.15 |
| 5,562,738 A | 10/1996 | Boyd et al. | |
| 5,645,599 A | 7/1997 | Samani | |
| 5,674,294 A | 10/1997 | Bainville et al. | |
| 5,674,296 A | 10/1997 | Bryan et al. | |
| 5,676,702 A | 10/1997 | Ratron | |
| 5,683,465 A | 11/1997 | Shinne et al. | |
| 5,824,093 A | 10/1998 | Ray et al. | |
| 5,824,094 A * | 10/1998 | Serhan et al. | 623/17.16 |
| 5,865,846 A | 2/1999 | Bryan et al. | |
| 5,888,226 A | 3/1999 | Rogozinski | |
| 5,893,889 A | 4/1999 | Harrington | |
| 5,958,314 A | 9/1999 | Draenert | |
| 5,976,186 A | 11/1999 | Bao et al. | |
| 6,110,210 A | 8/2000 | Norton | |
| 6,113,637 A | 9/2000 | Gill et al. | |
| 6,113,640 A | 9/2000 | Tormala | |
| 6,136,031 A | 10/2000 | Middleton | |
| 6,139,579 A * | 10/2000 | Steffee et al. | 623/17.16 |
| 6,156,067 A | 12/2000 | Bryan et al. | |
| 6,162,252 A * | 12/2000 | Kuras et al. | 623/17.16 |
| 6,176,881 B1 | 1/2001 | Schar | |
| 6,187,043 B1 * | 2/2001 | Ledergerber | 623/8 |
| 6,187,048 B1 | 2/2001 | Milner et al. | |
| 6,224,607 B1 | 5/2001 | Michelson | |
| 6,296,664 B1 | 10/2001 | Middleton | |
| 6,315,797 B1 | 11/2001 | Middleton | |
| 6,348,071 B1 * | 2/2002 | Steffee et al. | 623/17.15 |
| 6,368,350 B1 * | 4/2002 | Erickson et al. | 623/17.14 |
| 6,395,032 B1 | 5/2002 | Gauchet | |
| 6,419,704 B1 * | 7/2002 | Ferree | 623/17.12 |
| 6,419,706 B1 | 7/2002 | Graf | |
| 6,482,234 B1 | 11/2002 | Weber et al. | |
| 6,527,804 B1 | 3/2003 | Gauchet et al. | |
| 6,533,818 B1 | 3/2003 | Weber et al. | |
| 6,548,569 B1 | 4/2003 | Williams | |
| 6,579,320 B1 * | 6/2003 | Gauchet et al. | 623/17.15 |
| 6,579,321 B1 * | 6/2003 | Gordon et al. | 623/17.16 |
| 6,582,466 B1 | 6/2003 | Gauchet | |
| 6,582,467 B1 | 6/2003 | Teitelbaum et al. | |
| 6,582,468 B1 | 6/2003 | Gauchet | |
| 6,592,624 B1 * | 7/2003 | Fraser et al. | 623/17.16 |
| 6,607,558 B2 * | 8/2003 | Kuras | 623/17.16 |
| 6,626,943 B2 | 9/2003 | Eberlein | |
| 6,645,248 B2 * | 11/2003 | Casutt | 623/17.12 |
| 6,656,224 B2 * | 12/2003 | Middleton | 623/17.16 |
| 6,669,732 B2 * | 12/2003 | Serhan et al. | 623/17.16 |
| 6,682,562 B2 | 1/2004 | Viart et al. | |
| 6,726,720 B2 * | 4/2004 | Ross et al. | 623/17.13 |
| 6,733,532 B1 | 5/2004 | Gauchet | |
| 6,740,093 B2 | 5/2004 | Hochschuler | |
| 6,740,118 B2 * | 5/2004 | Eisermann et al. | 623/17.14 |
| 6,749,635 B1 | 6/2004 | Bryan | |
| 6,793,678 B2 | 9/2004 | Hawkins | |
| 6,893,465 B2 * | 5/2005 | Huang | 623/17.12 |
| 7,169,181 B2 * | 1/2007 | Kuras | 623/17.11 |
| 7,250,060 B2 * | 7/2007 | Trieu | 623/17.15 |
| 7,255,714 B2 | 8/2007 | Malek | |
| 7,520,900 B2 | 4/2009 | Trieu | |
| 7,776,072 B2 | 8/2010 | Lee | |
| 7,794,501 B2 | 9/2010 | Edie | |
| 7,905,921 B2 | 3/2011 | Kim | |
| 8,182,534 B2 | 5/2012 | Ogilvie | |
| 8,187,330 B2 * | 5/2012 | Gimbel et al. | 623/17.15 |
| 8,206,449 B2 * | 6/2012 | Jansen et al. | 623/17.16 |
| 2001/0016773 A1 * | 8/2001 | Serhan et al. | 623/17.15 |
| 2001/0032017 A1 | 10/2001 | Alfaro et al. | |
| 2001/0051829 A1 | 12/2001 | Middleton | |
| 2002/0022888 A1 * | 2/2002 | Serhan et al. | 623/17.16 |
| 2002/0077533 A1 | 6/2002 | Bieger et al. | |
| 2002/0077701 A1 | 6/2002 | Kuslich | |
| 2003/0045939 A1 | 3/2003 | Casutt | |
| 2003/0074066 A1 * | 4/2003 | Errico et al. | 623/17.14 |
| 2003/0078667 A1 | 4/2003 | Manasas et al. | |
| 2003/0100951 A1 * | 5/2003 | Serhan et al. | 623/17.16 |
| 2003/0135277 A1 * | 7/2003 | Bryan et al. | 623/17.12 |
| 2003/0164172 A1 | 9/2003 | Chumas et al. | |
| 2003/0208271 A1 * | 11/2003 | Kuras | 623/17.11 |
| 2003/0236526 A1 | 12/2003 | Van Hoeck | |
| 2004/0002711 A1 | 1/2004 | Berry | |
| 2004/0103903 A1 | 6/2004 | Falahee | |
| 2004/0122517 A1 * | 6/2004 | Kuras | 623/17.11 |
| 2004/0122518 A1 * | 6/2004 | Rhoda | 623/17.11 |
| 2004/0143332 A1 * | 7/2004 | Krueger et al. | 623/17.14 |
| 2004/0162563 A1 | 8/2004 | Michelson | |
| 2004/0167626 A1 * | 8/2004 | Geremakis et al. | 623/17.15 |
| 2004/0193273 A1 * | 9/2004 | Huang | 623/17.12 |
| 2004/0215197 A1 | 10/2004 | Smith et al. | |
| 2004/0220668 A1 * | 11/2004 | Eisermann et al. | 623/17.11 |
| 2004/0249462 A1 * | 12/2004 | Huang | 623/17.13 |
| 2004/0267367 A1 | 12/2004 | O'Neil | |
| 2005/0015150 A1 * | 1/2005 | Lee | 623/17.12 |
| 2005/0027300 A1 | 2/2005 | Hawkins et al. | |
| 2005/0071007 A1 | 3/2005 | Malek | |
| 2005/0080487 A1 | 4/2005 | Schultz et al. | |
| 2005/0131544 A1 * | 6/2005 | Kuras et al. | 623/17.13 |
| 2005/0273111 A1 | 12/2005 | Ferree | |
| 2006/0079907 A1 | 4/2006 | Boettiger | |
| 2006/0111783 A1 | 5/2006 | Aflatoon | |
| 2006/0190082 A1 | 8/2006 | Keller | |
| 2006/0229724 A1 * | 10/2006 | Lechmann et al. | 623/17.11 |
| 2006/0241767 A1 | 10/2006 | Doty | |
| 2006/0265075 A1 | 11/2006 | Baumgartner et al. | |
| 2006/0276800 A1 | 12/2006 | Lee et al. | |
| 2006/0276900 A1 | 12/2006 | Carpenter | |
| 2007/0032873 A1 | 2/2007 | Pisharodi | |
| 2007/0032874 A1 | 2/2007 | Lee | |
| 2008/0046082 A1 | 2/2008 | Lee | |
| 2008/0077243 A1 | 3/2008 | Lee | |
| 2008/0306609 A1 | 12/2008 | Lee et al. | |
| 2009/0030521 A1 | 1/2009 | Lee | |
| 2009/0088853 A1 | 4/2009 | Ogilvie | |
| 2009/0216329 A1 | 8/2009 | Lee | |
| 2012/0059481 A1 * | 3/2012 | Abernathie et al. | 623/17.16 |
| 2012/0101579 A1 * | 4/2012 | de Villiers et al. | 623/17.16 |

FOREIGN PATENT DOCUMENTS

| | | |
|---|---|---|
| EP | 0 566 810 | 10/1993 |
| EP | 0 642 775 | 3/1995 |
| FR | 2 784 291 | 4/2000 |
| GB | 1 496 804 | 1/1978 |
| GB | 1 589 192 | 5/1981 |
| JP | 03-501810 T | 4/1991 |
| JP | 06-285099 A | 11/1994 |
| JP | 08-004606 B | 1/1996 |
| JP | 3007903 B2 | 2/2000 |
| WO | WO 89/03663 | 5/1989 |

| | | |
|---|---|---|
| WO | WO 90/11740 | 10/1990 |
| WO | WO 95/19153 | 7/1995 |
| WO | WO 99/22675 | 5/1999 |
| WO | WO 03/090650 | 11/2003 |
| WO | WO 2004/033516 | 4/2004 |
| WO | WO 2004/039291 | 5/2004 |
| WO | WO 2004/054453 | 7/2004 |
| WO | WO 2005/016172 | 2/2005 |
| WO | WO 2005/072660 | 8/2005 |
| WO | WO 2005/011523 | 10/2005 |
| WO | WO 2005/007041 | 12/2005 |
| WO | WO 2006/078662 | 7/2006 |
| WO | WO 2006/078663 | 7/2006 |
| WO | WO 2006/081421 | 12/2006 |
| WO | WO 2007/050644 | 5/2007 |

OTHER PUBLICATIONS

Fraser RD et al., Spine J. 2004, 4(6S): 245s-251s.
Szpalski M, Eur. Spine J. (2000), 11(Supp1.2): S65-84.
McAfee, P. et al., Spine J. 4:48s, 2004.
Hawkins MV et al., J. Orthop. Res. 12: 119-127, 1994.
Closkey RF et al., Spine 18(8): 1011-1015, 1993.
Langrana NA et al., Spine J. 4 (2004), 245S-251S.

* cited by examiner

ENDPLATE FOR AN INTERVERTEBRAL PROSTHESIS AND PROSTHESIS INCORPORATING THE SAME

CROSS REFERENCE TO RELATED APPLICATION

This application claims the benefit of U.S. Provisional Application No. 61/050,554, filed May 5, 2008, the entire disclosure of which is incorporated herein by reference.

BACKGROUND OF THE INVENTION

1. Field of the Invention

This invention relates to prostheses for replacing natural intervertebral discs and more particularly to endplates incorporated into such prostheses for contacting the bodies of vertebrae adjacent to such prostheses.

2. Background Art

Prostheses for replacing a damaged or degenerated intervertebral disc often incorporate a relatively hard endplate intended to contact the body of an adjacent vertebra, fix the prosthesis in its intended location, and transfer spinal loads to other elements of the prosthesis.

A great variety of designs for such vertebra-contacting endplates have been proposed, and many have been experimentally implanted in patients, and thereby tested for safety and efficacy. However, the mechanical and physiological requirements for satisfactory performance of such endplates are complex and not easily met. Furthermore, the surgical procedures for implantation of intervertebral prostheses are complex and place great demands on the skill of the surgeon, which in turn establishes a need for prostheses adapted for uncomplicated implantation. Consequently, development of satisfactory designs for such prostheses, and, in particular, for the vertebra-contacting endplates thereof, has required much effort over along period of time. Furthermore, because of the great variation among individual patients and the many and various possible disorders afflicting the natural intervertebral disc, it is desirable for the surgeon to have a variety of designs available for selection to treat a particular patient.

Accordingly, a need has continued to exist for intervertebral prostheses having endplates that are well adapted for ease of implantation and for effective performance after implantation to relieve the distress of disorders of the natural intervertebral disc.

SUMMARY OF THE INVENTION

In accordance with one its principal aspects, the intervertebral disc prosthesis endplate of the invention includes a plate member, sized and configured to fit within an intervertebral space of a human spinal motion segment. The plate member includes an upper peripheral rim portion with an anterior region and a posterior region, and an elevated region within the upper peripheral rim portion. The elevated region has an antero-posterior dimension and a transverse dimension different from the antero-posterior dimension, and is bounded by a wall projecting upward from the peripheral rim portion. The wall has laterally opposite side portions defined by arcs terminating in sagittal planes of the plate member which are symmetrical with respect to a coronal plane of said base plate. The elevated region has an anterior portion and a posterior portion, the posterior portion having a generally planar upper surface and the anterior portion being recessed with respect to the upper surface of the posterior portion, with a coating to promote bone ingrowth being provided on the anterior portion, but not on the posterior portion, of the elevated region.

The coating, which may be a beaded layer or equivalent porous layer, is provided for bone ingrowth, while the relatively smooth posterior region provides for ease of implantation. The elevated region or dome is bounded by a wall rising from the rim, typically relatively steeply. The wall has generally straight transverse anterior and posterior portions connected by lateral curved portions. Optionally, the anterior portion of the endplate may be provided with one or more upstanding fins to engage the adjacent vertebral body for improved fixation and resistance to post-operative movement and/or expulsion of the prosthesis.

Accordingly, from one point of view, the invention provides an endplate for an intervertebral prosthesis that is adapted for secure fixation of the prosthesis within the intervertebral space.

From another point of view, the invention provides an endplate for an intervertebral disc prosthesis that is adapted for easy implantation within the intervertebral space after partial or total excision of a damaged or degenerated natural intervertebral disc.

From another point of view, the invention provides an endplate for an intervertebral disc prosthesis that may be implanted from an anterior surgical approach, an anterior-lateral surgical approach, or a lateral surgical approach.

From another point of view, the invention provides an endplate for an intervertebral disc prosthesis having a fin aligned in an anterior-posterior direction, but extending only over an anterior portion of the upper surface of the endplate.

From another point of view, the invention provides a finned endplate for an intervertebral disc prosthesis that can provide greater ease of insertion as compared with a prosthesis having an anterior-posterior fin extending generally over the entire anterior-posterior dimension of the endplate.

From another point of view, the invention provides an endplate for an intervertebral disc prosthesis having a generally anteriorly positioned partial antero-posterior fin that can provide post-implantation stability generally equivalent to that of a prosthesis endplate having a complete antero-posterior fin.

From another point of view, the present invention provides an intervertebral disc prosthesis incorporating at least one endplate as discussed above.

In accordance with another of its principal aspects, the present invention provides an endplate for an intervertebral disc prosthesis, comprising a plate member sized and configured to fit within an intervertebral space of a human spinal motion segment, the plate member including an upper peripheral rim portion having an anterior region and a posterior region, and an elevated region within the upper peripheral rim portion. The elevated region is bounded by a wall projecting upward from the peripheral rim portion and has an anterior portion and a posterior portion, the posterior portion having a generally planar upper surface. The anterior portion, but not the posterior portion, is subjected to surface modification so as to provide bone ingrowth promoting structure having an upper surface substantially coplanar with the upper surface of the posterior portion of the elevated region.

Further aspects, features and advantages of the invention will be apparent from the description which follows and the accompanying drawings, which are provided for illustration only, and are not to be considered as limiting the scope of the invention.

DETAILED DESCRIPTION OF THE INVENTION AND PREFERRED EMBODIMENTS

The intervertebral prosthesis endplate of the invention may be incorporated into the intervertebral prostheses disclosed in copending U.S. patent application Ser. No. 12/239,559 filed Sep. 26, 2008, of which the inventor is a coinventor, the entire disclosure of which is incorporated herein by reference. Although the endplate of this invention incorporates a number of novel features in its vertebra-contacting surface, it may be incorporated into a complete intervertebral prosthesis using the structures and methods disclosed in U.S. patent application Ser. No. 12/239,559, as may be understood from the embodiments of the invention illustrated in the accompanying drawings.

Certain embodiments of the invention are illustrated in the accompanying drawings, which are intended to be illustrative and not limiting. As will be recognized by the skilled practitioner, an intervertebral prosthesis according to the invention typically will employ two endplates of the invention, adjacent to and contacting a superior and an inferior vertebra, respectively, of a spinal motion segment, and a core component located between the endplates and securely fastened thereto, as generally illustrated in FIGS. 9, 10, 13, and 14. Typically, the two endplates will be of identical construction, and the following description, wherein certain elements of the endplate are described as upper and lower, refers to the upper or superior of the two prosthesis endplates when the prosthesis is oriented for implantation in an intervertebral space. Such directional references are to be considered as defining the structure of the endplate and the relative spatial relationship of its constituent parts. The skilled practitioner will recognize that the lower or inferior endplate of the prosthesis will be inverted with respect to the upper or superior endplate, and the relative spatial directions will be modified accordingly.

Figure 1:
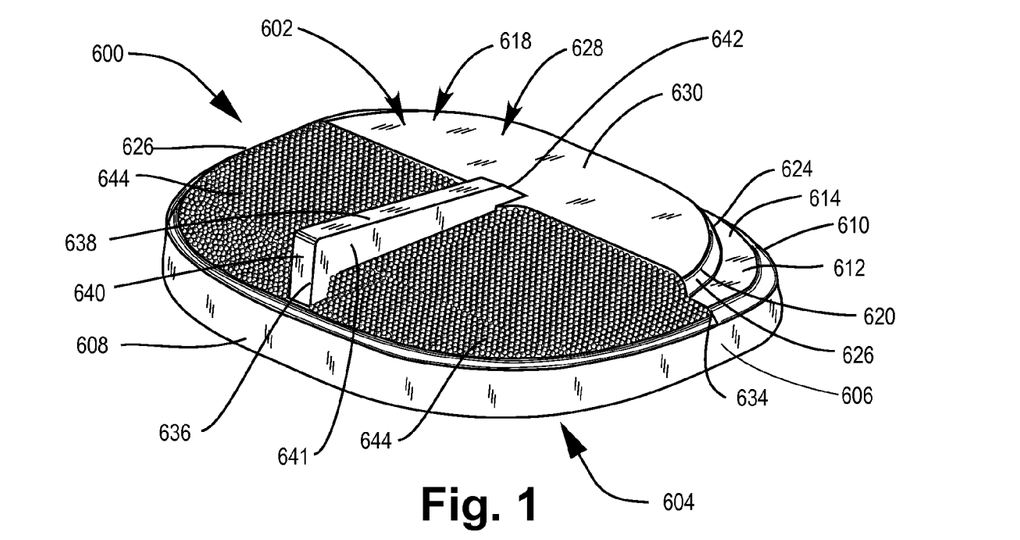
FIG. 1 is a perspective view of an intervertebral disc prosthesis endplate according to the invention.
Figure 2:
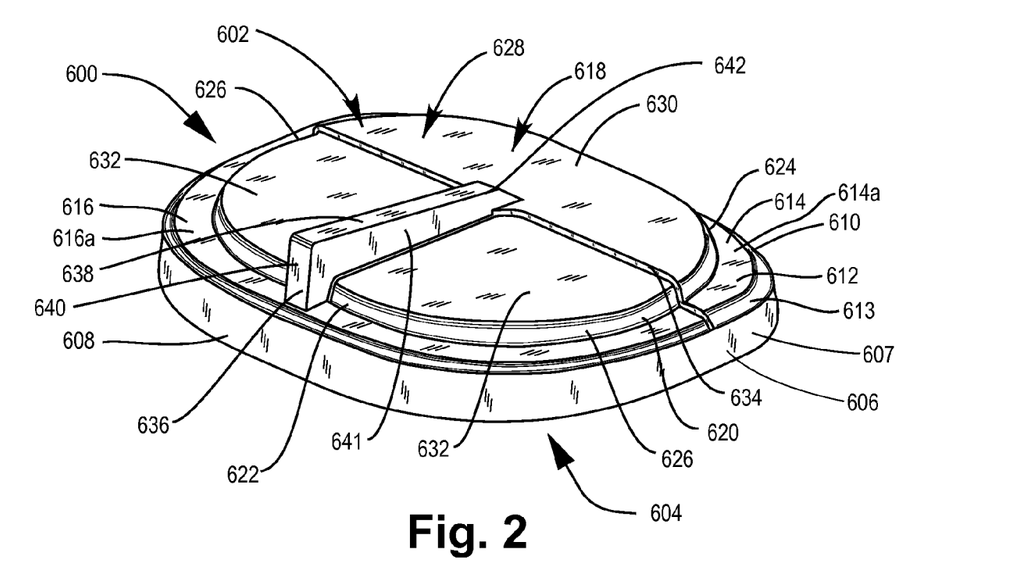
FIG. 2 is a perspective view of the basic body of the intervertebral disc endplate of FIG. 1 devoid of the porous coating of beads on the anterior portion.
Figures 3, 4:
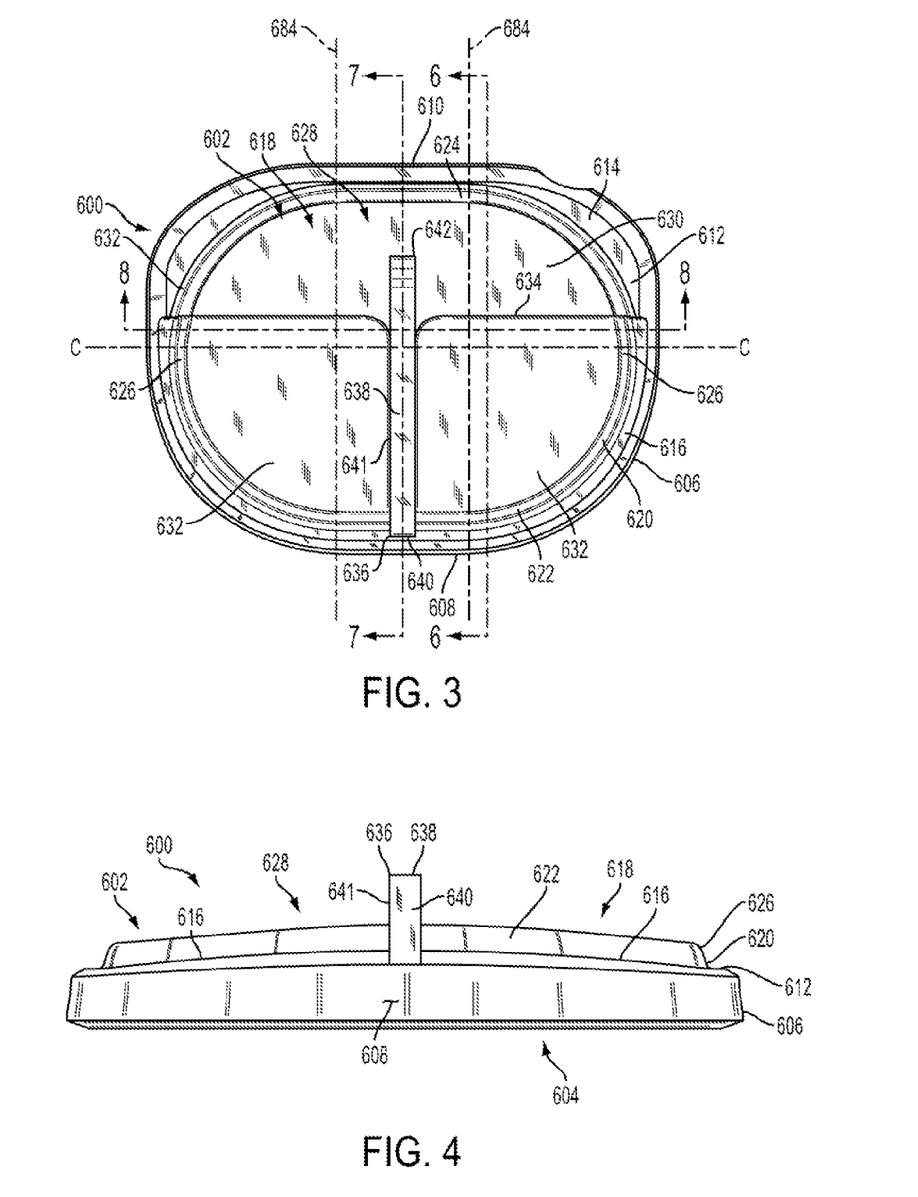
FIG. 3 is a plan view of the intervertebral disc endplate of FIG. 2.
FIG. 4 is an anterior elevational view of the intervertebral disc endplate of FIG. 2.

FIG. 1 illustrates a completed endplate 600 of the invention provided with a beaded surface 644 which provides a relatively porous region for encouraging ingrowth of bony tissue for secure fixation of the prosthesis to adjacent vertebrae. FIG. 2 illustrates the prosthesis endplate before the beaded area has been formed to show the underlying structural features of the upper surface 602 of the endplate 600. The prosthesis endplate 600 has an upper surface 602 and a bottom surface 604. The prosthesis 600 comprises a plate member (or baseplate) 606, having an anterior edge 608 and a posterior edge 610. The plate member 606 has a circumferential upper rim 612, divided into a posterior region 614 and an anterior region 616 by an intermediate step 634. In the form shown, upper rim 612 includes a planar posterior inner region 614a and a planar anterior inner region 616a within a chamfered or contoured region 613 connecting the inner regions with the sidewall 607 of the plate member 606.

The endplate 600 is provided with a central elevated region or dome 618, occupying a major portion of the upper surface 602 of the endplate 600, and having a circumferential wall 620 rising from the rim 612. The wall of the elevated region or dome 618 has an anterior portion 622 and a posterior portion 624, both of which are generally straight and extend transversely across a substantial portion of the upper surface 602 of the endplate 600. The anterior portion 622 and posterior portion 624 are at least substantially parallel to each other and to a lateral center line C-C of the endplate, and are connected at their lateral ends by curved lateral walls 626, generally in the shape of circular arcs terminating in sagittal planes 684, to form a complete circumferential wall 620 of the elevated region 616. Such an endplate having an upper peripheral rim and central elevated region or dome is disclosed in copending U.S. patent application Ser. No. 12/091,296, the entire disclosure of which is incorporated herein by reference and in copending U.S. patent application Ser. No. 11/862,012, the entire disclosure of which is incorporated herein by reference.

The upper surface 628 of the elevated region 618 is divided by the generally transverse step 634 into a posterior region 630 and an anterior region 632. The posterior region 630 is generally smooth and substantially planar, and does not have a rough or porous or beaded surface. Thus, it is intended to be easily fitted into the posterior portion of the intervertebral space, formed by excision of the natural intervertebral disc, which can be difficult to access and prepare through a conventional anterior surgical approach. The anterior portion 632 of the upper surface 628 of the dome 618 is somewhat depressed or recessed relative to the posterior region 630, thus forming the intervening step 634. This anterior region 632 may be divided by an antero-posterior fin 636, and is provided with a porous surface, such as beaded surface 644, or other suitable surface intended to promote the ingrowth of bone after implantation of the prosthesis. The step 634 is preferably of sufficient height that the beads or other bone ingrowth promoting structure(s) do not protrude above the plane of the posterior region 630. Other bone ingrowth promoting structures can include plasma coatings, for example, as well as other conventional structures known for this purpose. Preferably, the bone ingrowth promoting structures provide a porous upper surface that is substantially coplanar with the upper surface of the posterior region 630. In one possible alternative, the anterior region 632 could be made coplanar with posterior region 630 and subjected to surface roughening or other surface modification to provide bone ingrowth promoting structures.

Figure 5:
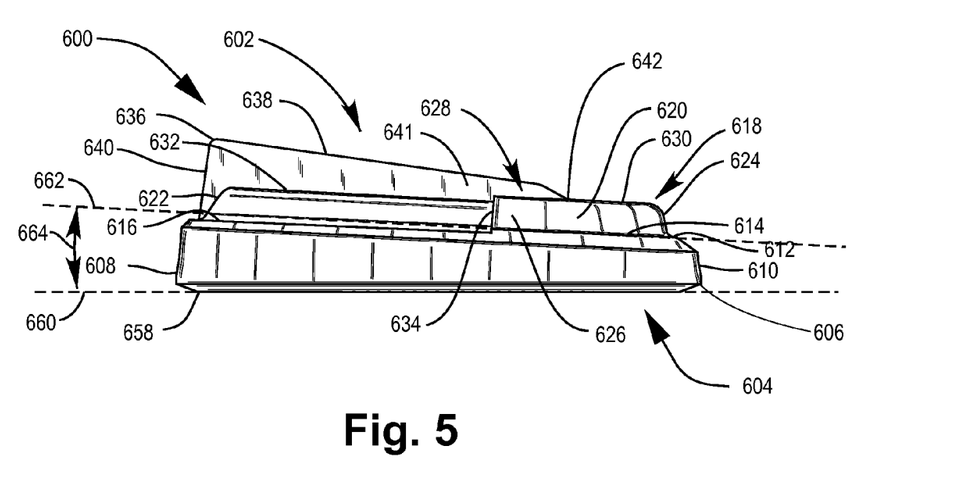
FIG. 5 is a left lateral elevational view of the intervertebral disc endplate of FIG. 2.
Figure 6:
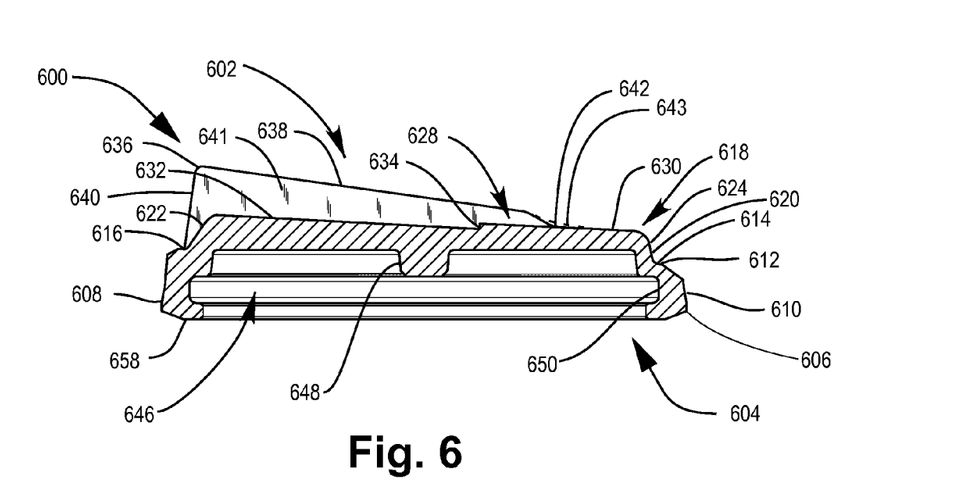
FIG. 6 is a cross-section taken at the line 6-6 in FIG. 3.
Figure 7:
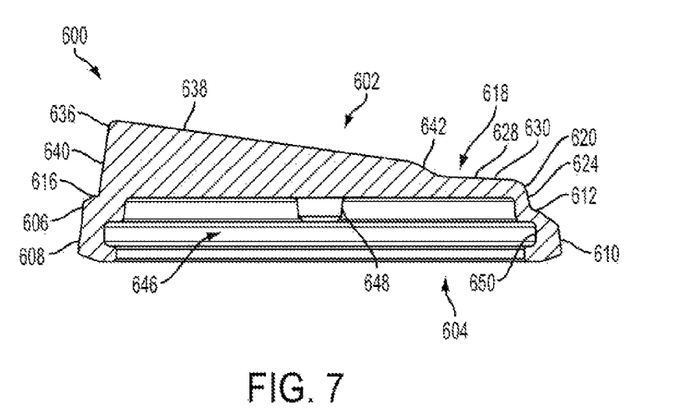
FIG. 7 is a cross-section taken at the line 7-7 in FIG. 3.
Figure 8:
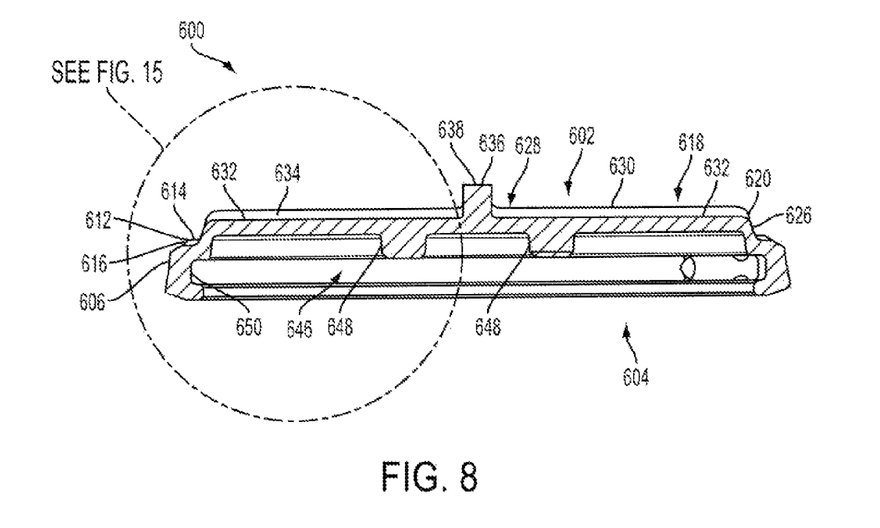
FIG. 8 is a cross-section taken at the line 8-8 in FIG. 3.
Figure 9:
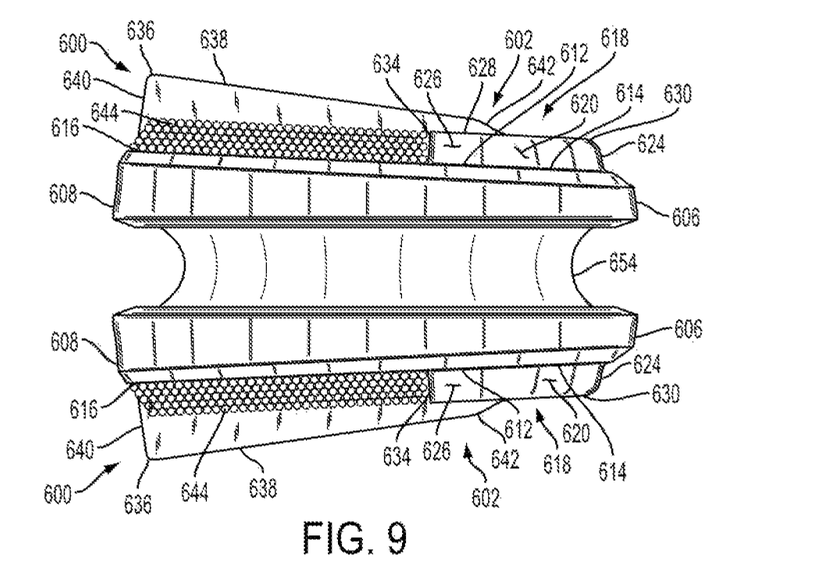
FIG. 9 is a lateral view of an intervertebral prosthesis incorporating upper and lower endplates according to the invention.
Figure 10:
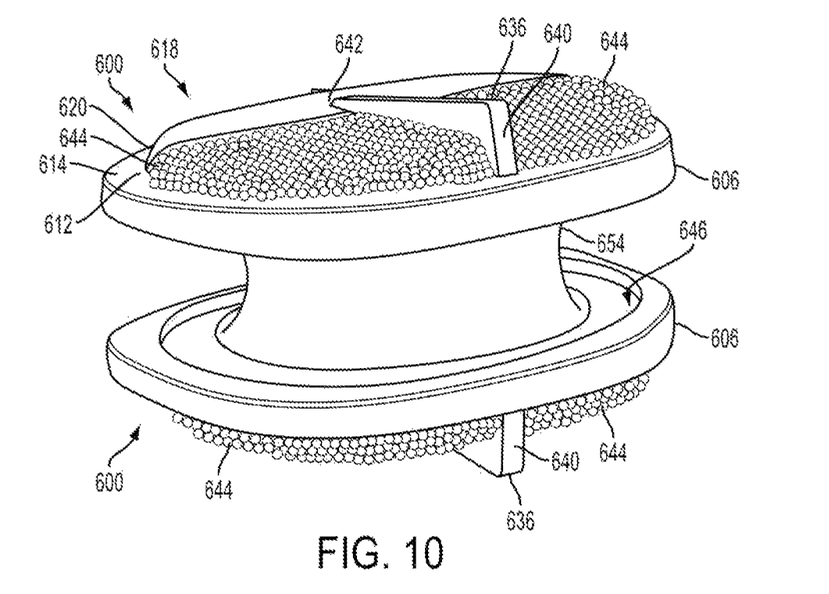
FIG. 10 is a perspective view of a prosthesis similar to that illustrated in FIG. 9.
Figure 11:
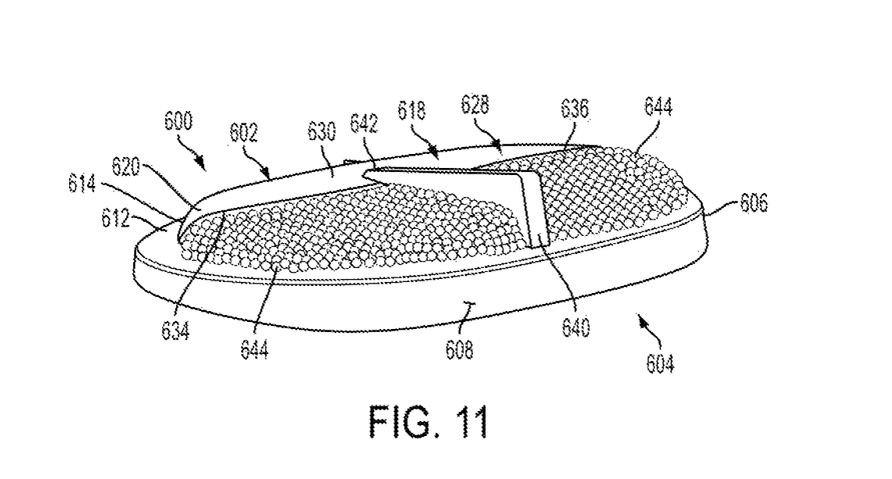
FIG. 11 is a perspective view of an endplate according to the invention.
Figure 12:
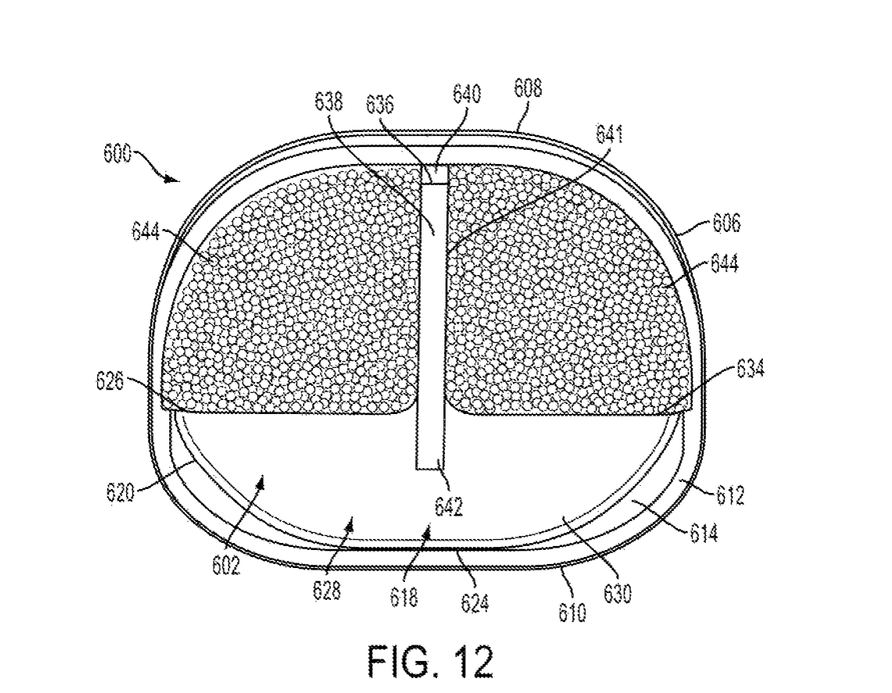
FIG. 12 is a plan view of the prosthesis endplate of FIG. 11.
Figure 13:
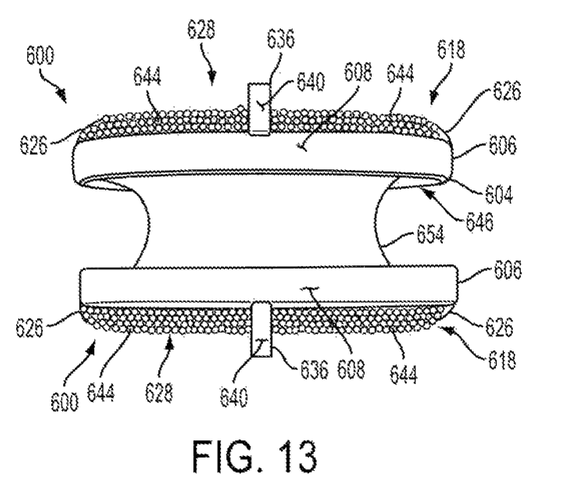
FIG. 13 is an anterior elevational view of a prosthesis of the invention incorporating endplates of the invention.
Figure 14:
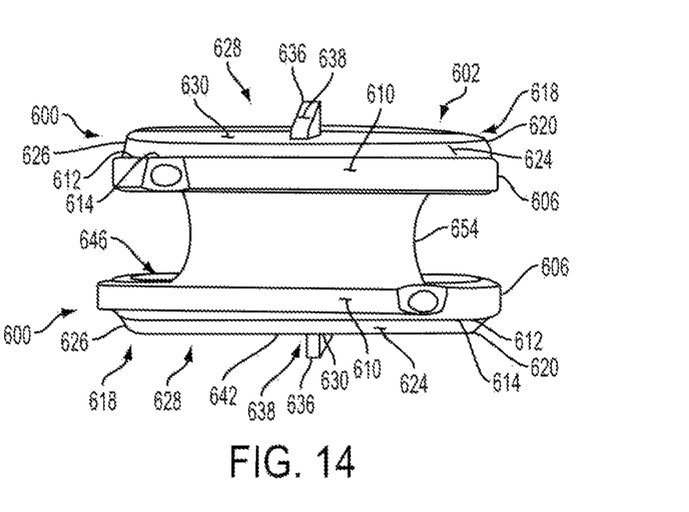
FIG. 14 is a posterior elevational view of a prosthesis of the invention incorporating endplates of the invention.
Figure 15:
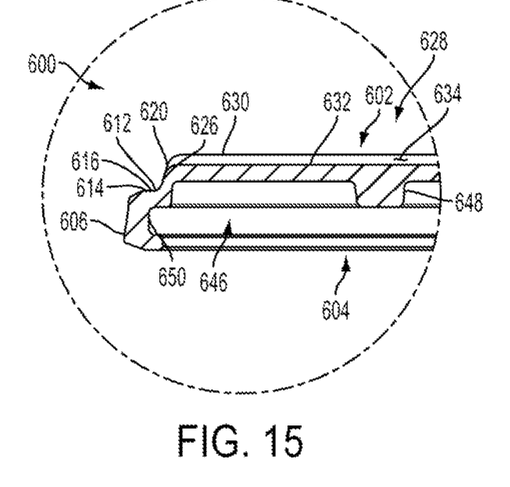
FIG. 15 is a detail view of the portion of the prosthesis endplate of the invention indicated by the dashed circle 15 in FIG. 8.
Figure 16:
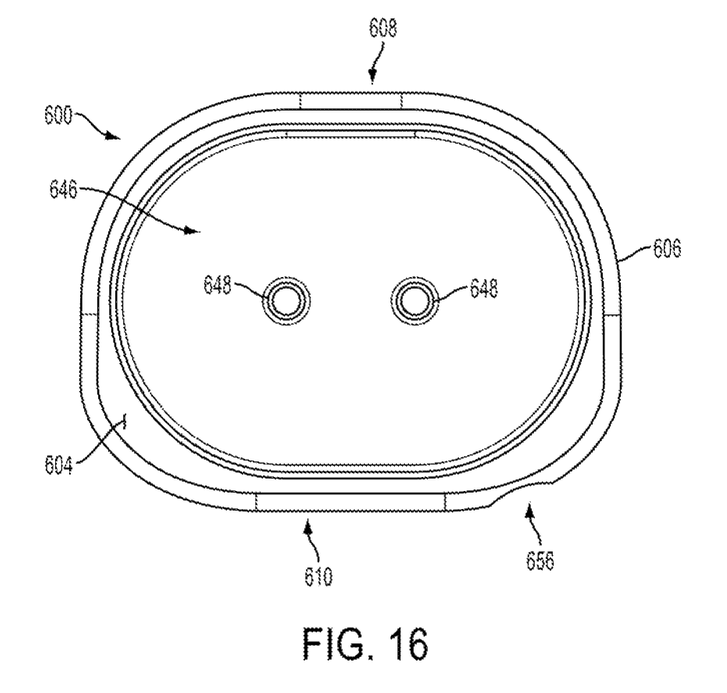
FIG. 16 is a bottom plan view of the intervertebral disc endplate body of FIG. 2.
Figure 17:
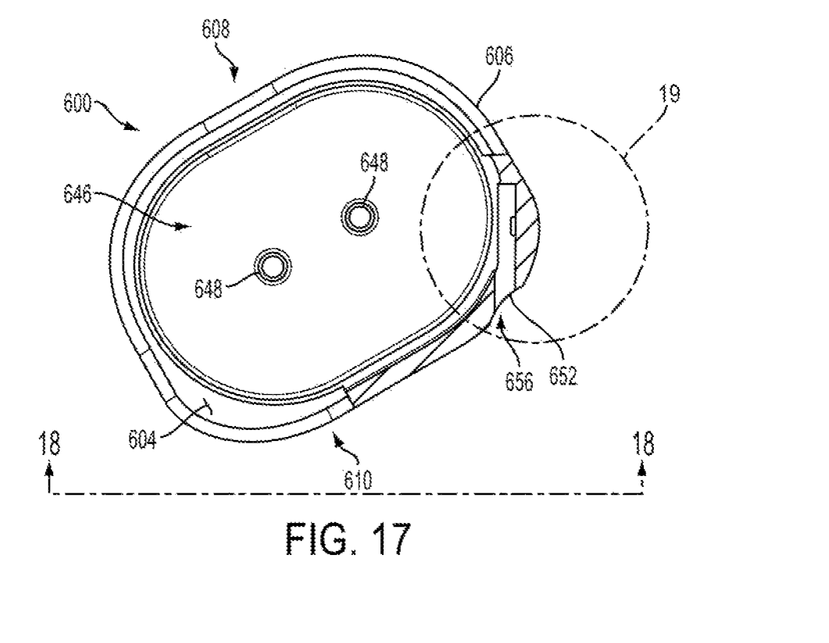
FIG. 17 is a bottom plan view similar to that of FIG. 16, rotated by 30 degrees and partially cut away along the line 17-17 in FIG. 18, to illustrate the insertion aperture in the rim of the plate member for inserting a retaining ring for fastening the endplate to a core in a prosthesis such as that illustrated in FIGS. 10, 13, and 14.
Figure 18:
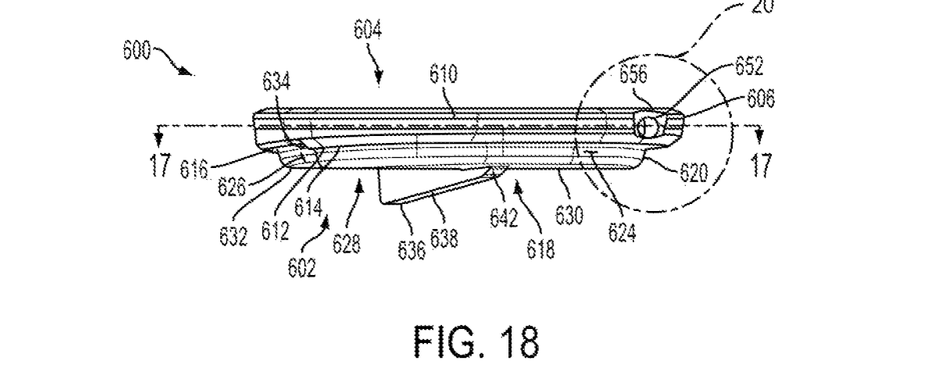
FIG. 18 is a view of the endplate as seen in the direction indicated by line 18-18 in FIG. 17, showing the insertion aperture for the retaining ring.

In order to provide for varying lordotic angles between the vertebrae adjacent to the prosthesis of the invention, the upper peripheral rim portion of endplate, together with the upper surface of the elevated region supported on the rim, may optionally be inclined to provide a greater axial height at the anterior edge of the prosthesis endplate than at the posterior edge. Thus, as shown, e.g., in FIGS. 5 and 6, the plate member 606 has a lower periphery 658 disposed in a first plane 660, and the anterior region 616 and the posterior region 614 of the upper peripheral rim portion 612 of the plate member 606 are substantially parallel to a second plane 662 oriented at an anteriorly opening angle 664 with respect to the first plane 660 of the lower periphery 658. The anterior opening angle 664 may typically vary from 0 degrees to about 7.5 degrees. FIG. 5 illustrates an embodiment wherein the anterior opening angle 664 is about 3 degrees.

A fin 636 may be provided positioned generally on the medial center line of the endplate to provide additional stability to the implanted prosthesis. The fin is designed and configured to mate with a corresponding recess surgically formed in the adjacent vertebral body to provide stability against expulsion of the implanted prosthesis and to resist torsional displacement of the endplate with respect to the adjacent vertebral body. The fin has an upper surface 638, an anterior end 640 and lateral surfaces 641. The height of the fin decreases from its anterior end to its posterior end 642, where the height of the fin becomes zero and the upper surface of the fin merges with the upper surface of the plate member posterior region 630. The upper surface of posterior end 642 of the fin may be radiused to merge more gradually and smoothly into the upper surface of region 630, as indicated by dashed line 643 in FIG. 6. The anterior end 640 of the fin 636 is generally positioned, as shown, slightly posterior to the anterior edge 608 of the plate member 606 to allow at least a portion of the upper rim 612 of the plate member 606 to contact the firm cortical bone region of the adjacent vertebra. The posterior end 642 of the fin 636 is positioned somewhat anteriorly to the posterior wall 624 of the dome 618. Such a termination of the fin 636 allows for a more convenient surgical preparation and implantation of the prosthesis as compared with an endplate having a fin extending substantially to the posterior edge thereof. In particular, providing a fin having anterior and posterior ends positioned inward from the anterior and posterior edges of the plate member allows the recess in the adjacent vertebra for receiving the fin to be formed only in the central region of the vertebra, sparing the anterior cortical rim. Apparatus for forming a recess inside the cortical rim of a vertebra is disclosed, e.g., in U.S. patent application Ser. No. 11/862,012. Thus, a prosthesis having an endplate of the invention can be implanted with its fin received in such an interior recess, whereby the interaction of the fin with the intact anterior rim of the vertebra, with its dense and strong cortical bone, provides superior resistance to expulsion of the prosthesis.

Figure 19:
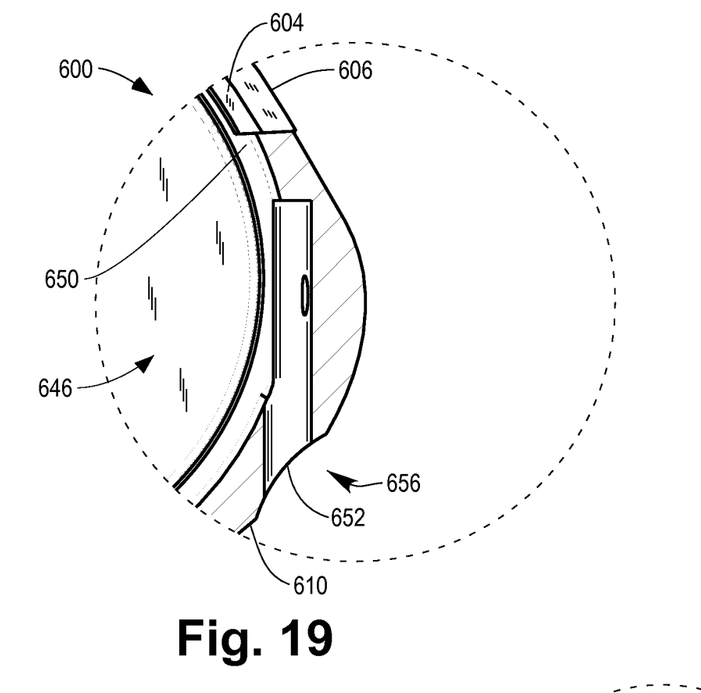
FIG. 19 is a detail section of the retaining ring insertion aperture as indicated by the dashed circle 19 in FIG. 17.
Figure 20:
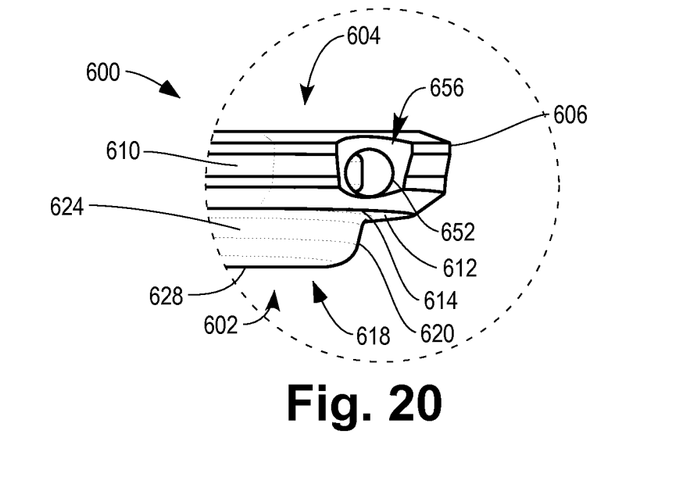
FIG. 20 is a detail section of the retaining ring insertion aperture as indicated by the dashed circle 20 in FIG. 18.

In the illustrated embodiment of the prosthesis endplate 600, the bottom surface 604 of the endplate is provided with a recess 646 and associated structure for attachment to an elastomeric core element provided with a perforated coupling plate as described in U.S. patent application Ser. No. 12/239,559. Accordingly, the illustrated embodiment of the inventive endplate is provided with support pillars 648 that support the coupling plate, a groove 650 for a retaining ring such as that of U.S. patent application Ser. No. 12/239,559 or equivalent retaining ring, and an aperture or hole 652 for inserting the retaining ring. The posterior edge 610 of the plate member 606 is provided, in the illustrated embodiment, with a recess 656 surrounding the insertion aperture 652 in order to avoid or minimize, to the extent possible, any contact of a protruding end of the retaining ring with adjacent tissue. Such structures fitting the retaining ring are shown in FIGS. 19 and 20, with details in FIGS. 21 and 22.

A prosthesis of the invention typically will include a pair of endplates 600 and a core 654, as shown in FIGS. 9, 10, 13, and 14. The core 654 may be an elastomeric core with embedded perforated coupling plate as disclosed in U.S. patent application Ser. No. 12/239,559.

Accordingly, a prosthesis having an endplate of the invention can be implanted by a procedure in which the defective intervertebral disc of a spinal motion segment is at least partially excised, appropriate distraction is performed, a seat for the elevated region (and fin if provided) is prepared, the prosthesis is implanted between the vertebrae of the spinal motion segment, and the vertebrae are allowed to resume their normal anatomical position, whereby the elevated region (and fin if provided) of the endplate becomes seated in the prepared recess, and the peripheral rim region contacts the cortex of the adjacent vertebra. A prosthesis so implanted will be well integrated with the spinal motion segment and will be particularly resistant to anterior expulsion by reason of the intact anterior vertebral rim.

The invention having been described in terms of certain disclosed embodiments, it will be evident to the skilled practitioner that various changes and modifications can be made thereto without departing from the substance and scope of the invention.

I claim:

1. An endplate for an intervertebral disc prosthesis, comprising:
    a plate member sized and configured to fit within an intervertebral space of a human spinal motion segment,
    said plate member including an upper peripheral rim portion having an anterior region and a posterior region, and an elevated region within said upper peripheral rim portion,
    said elevated region having an antero-posterior dimension and a transverse dimension different from said antero-posterior dimension, said elevated region further being bounded by a wall projecting upward from said peripheral rim portion,
    said wall having laterally opposite side portions defined by arcs terminating in sagittal planes of said plate member and symmetrical with respect to a coronal plane of said plate member,
    said elevated region having an anterior portion and a posterior portion, said posterior portion having a generally planar upper surface and said anterior portion being recessed with respect to said upper surface of said posterior portion,
    a coating which is effective to promote bone ingrowth being provided on said anterior portion, but not on said posterior portion, of the elevated region, wherein said coating has an upper surface substantially coplanar with said upper surface of said posterior portion of the elevated region.

2. The endplate of claim 1, wherein said endplate has an upstanding fin.

3. The endplate of claim 2 wherein said posterior end of said fin is disposed on said posterior portion of said elevated region.

4. The endplate of claim 2, wherein said fin decreases in height from one end to another end thereof.

5. The endplate of claim 1, wherein said endplate has an upstanding fin located generally in a median plane of said plate member, said fin having anterior end and a posterior end and an antero-posterior dimension less than an antero-posterior dimension of said plate member, said anterior end of said fin being located generally adjacent to an anterior edge of said plate member.

6. The endplate of claim 5, wherein said fin has an axial height that decreases from said anterior end to said posterior end.

7. The endplate of claim 1, wherein said endplate has an upstanding fin located generally in a median plane of said plate member, said fin having anterior end and a posterior end and an antero-posterior dimension less than an antero-posterior dimension of said plate member, said anterior end of said fin being located generally adjacent to an anterior edge of said plate member.

8. The endplate of claim 7, wherein said fin has a height that decreases from said anterior end to said posterior end.

9. The endplate of claim 1, wherein said coating is a beaded coating or a plasma coating.

10. The endplate of claim 1, wherein said transverse dimension of the elevated region is greater than said antero-posterior dimension thereof.

11. The endplate of claim 1, wherein said anterior region of said upper peripheral rim portion is recessed with respect to said posterior region thereof and at least part of said anterior region of said upper peripheral rim portion is provided with said coating.

12. The endplate of claim 1, wherein said plate member has a lower periphery disposed substantially in a first plane, and said anterior region and said posterior region of said upper peripheral rim portion of said plate member include planar portions which are substantially parallel to a second plane oriented at an anteriorly opening angle from 0° to about 7.5° with respect to said plane of said lower periphery.

13. The endplate of claim 1, wherein wall has an anterior side portion and a posterior side portion, said anterior and posterior side portions extending transversely, being substantially parallel to each other, and being joined to said laterally opposite side portions.

14. An endplate for an intervertebral disc prosthesis, comprising:
a plate member sized and configured to fit within an intervertebral space of a human spinal motion segment,
said plate member including an upper peripheral rim portion having an anterior region and a posterior region, and an elevated region within said upper peripheral rim portion,
said elevated region having an antero-posterior dimension and a transverse dimension different from said antero-posterior dimension, said elevated region further being bounded by a wall projecting upward from said peripheral rim portion,
said wall having laterally opposite side portions defined by circular arcs, each of said circular arcs having a center located on a sagittal plane of said plate member;
said elevated region having an anterior portion and a posterior portion, said posterior portion having a generally planar upper surface and said anterior portion being recessed with respect to said upper surface of said posterior portion,
a coating which is effective to promote bone ingrowth being provided on said anterior portion, but not on said posterior portion, of the elevated region, wherein said coating has an upper surface substantially coplanar with said upper surface of said posterior portion of the elevated region.

15. The endplate of claim 14, wherein said endplate has an upstanding fin located generally in a median plane of said plate member, said fin having anterior end and a posterior end and an antero-posterior dimension less than an antero-posterior dimension of said plate member, said anterior end of said fin being located generally adjacent to an anterior edge of said plate member.

16. The endplate of claim 15, wherein said fin has a height that decreases from said anterior end to said posterior end.

17. The endplate of claim 15, wherein said posterior end of said fin is disposed on said posterior portion of said elevated region.

18. The endplate of claim 14, wherein said endplate has an upstanding fin.

19. The endplate of claim 18, wherein said fin decreases in height from one end to another end thereof.

20. The endplate of claim 14, wherein said endplate has an upstanding fin located generally in a median plane of said plate member, said fin having anterior end and a posterior end and an antero-posterior dimension less than an antero-posterior dimension of said plate member, said anterior end of said fin being located generally adjacent to an anterior edge of said plate member.

21. The endplate of claim 20, wherein said fin has a height that decreases from said anterior end to said posterior end.

22. The endplate of claim 14, wherein said coating is a beaded coating or a plasma coating.

23. The endplate of claim 14, wherein said transverse dimension of the elevated region is greater than said antero-posterior dimension thereof.

24. The endplate of claim 14, wherein said anterior region of said upper peripheral rim portion is recessed with respect to said posterior region thereof and at least part of said anterior region of said upper peripheral rim portion is provided with said coating.

25. The endplate of claim 14, wherein said plate member has a lower periphery disposed substantially in a first plane, and said anterior region and said posterior region of said upper peripheral rim portion of said plate member include planar portions which are substantially parallel to a second plane oriented at an anteriorly opening angle from 0° to about 7.5° with respect to said plane of said lower periphery.

26. The endplate of claim 14, wherein wall has an anterior side portion and a posterior side portion, said anterior and posterior side portions extending transversely, being substantially parallel to each other, and being joined to said laterally opposite side portions.

27. An endplate for an intervertebral disc prosthesis, comprising:
a plate member sized and configured to fit within an intervertebral space of a human spinal motion segment,
said plate member including an upper peripheral rim portion having an anterior region and a posterior region, and an elevated region within said upper peripheral rim portion,
said elevated region being bounded by a wall projecting upward from said peripheral rim portion,
said elevated region having an anterior portion and a posterior portion, said posterior portion having a generally planar upper surface and said anterior portion being recessed with respect to said upper surface of said posterior portion, a coating which is effective to promote bone ingrowth being provided on said anterior portion, but not on said posterior portion, of the elevated region, wherein said coating has an upper surface substantially coplanar with said upper surface of said posterior portion of the elevated region.

28. The endplate of claim 27, wherein said endplate has an upstanding fin located generally in a median plane of said plate member, said fin having anterior end and a posterior end and an antero-posterior dimension less than an antero-posterior dimension of said plate member, said anterior end of said fin being located generally adjacent to an anterior edge of said plate member.

29. The endplate of claim 28, wherein said fin has a height that decreases from said anterior end to said posterior end.

30. The endplate of claim 28, wherein said posterior end of said fin is disposed on said posterior portion of said elevated region.

31. The endplate of claim 27, wherein said endplate has an upstanding fin.

32. The endplate of claim 31, wherein said fin decreases in height from one end to another end thereof.

33. The endplate of claim 27, wherein said coating is a beaded coating or a plasma coating.

34. An endplate for an intervertebral disc prosthesis, comprising:
    a plate member sized and configured to fit within an intervertebral space of a human spinal motion segment,
    said plate member including an upper peripheral rim portion having an anterior region and a posterior region, and an elevated region within said upper peripheral rim portion,
    said elevated region being bounded by a wall projecting upward from said peripheral rim portion,
    said elevated region having an anterior portion and a posterior portion, said posterior portion having a generally planar upper surface,
    said anterior portion, but not said posterior portion, being subjected to surface modification so as to provide bone ingrowth promoting structure having an upper surface substantially coplanar with said upper surface of said posterior portion of the elevated region.

35. The endplate of claim 34, wherein said bone ingrowth promoting structure includes a beaded coating, a plasma coating, or a roughened surface area.

36. An intervertebral disc prosthesis, comprising an elastomeric core and a pair of prosthesis endplates coupled to said core, at least one of said endplates comprising:
    a plate member sized and configured to fit within an intervertebral space of a human spinal motion segment,
    said plate member including an upper peripheral rim portion having an anterior region and a posterior region, and an elevated region within said upper peripheral rim portion,
    said elevated region having an antero-posterior dimension and a transverse dimension different from said antero-posterior dimension, said elevated region further being bounded by a wall projecting upward from said peripheral rim portion,
    said wall having laterally opposite side portions defined by circular arcs each of said circular arcs having a center located on a sagittal plane of said plate member;
    said elevated region having an anterior portion and a posterior portion, said posterior portion having a generally planar upper surface and said anterior portion being recessed with respect to said upper surface of said posterior portion,
    a coating which is effective to promote bone ingrowth being provided on said anterior portion, but not on said posterior portion, of the elevated region, wherein said coating has an upper surface substantially coplanar with said upper surface of said posterior portion of the elevated region.

37. An intervertebral disc prosthesis, comprising an elastomeric core and a pair of prosthesis endplates coupled to said core, at least one of said endplates comprising:
    a plate member sized and configured to fit within an intervertebral space of a human spinal motion segment,
    said plate member including an upper peripheral rim portion having an anterior region and a posterior region, and an elevated region within said upper peripheral rim portion,
    said elevated region having an antero-posterior dimension and a transverse dimension different from said antero-posterior dimension, said elevated region further being bounded by a wall projecting upward from said peripheral rim portion,
    said wall having laterally opposite side portions defined by arcs terminating in sagittal planes of said plate member and symmetrical with respect to a coronal plane of said plate member,
    said elevated region having an anterior portion and a posterior portion, said posterior portion having a generally planar upper surface and said anterior portion being recessed with respect to said upper surface of said posterior portion,
    a coating which is effective to promote bone ingrowth being provided on said anterior portion, but not on said posterior portion, of the elevated region, wherein said coating has an upper surface substantially coplanar with said upper surface of said posterior portion of the elevated region.

* * * * *